(12) United States Patent
Silva

(10) Patent No.: US 6,478,580 B1
(45) Date of Patent: Nov. 12, 2002

(54) COORDINATIVE DENTAL DIE INTERLOCKING SYSTEM

(76) Inventor: Tyrone A. Silva, 3315 NW. 79 Ave., Margate, FL (US) 33063

( * ) Notice: Subject to any disclaimer, the term of this patent is extended or adjusted under 35 U.S.C. 154(b) by 0 days.

(21) Appl. No.: 09/871,092

(22) Filed: May 31, 2001

(51) Int. Cl.7 ................................................ A61C 19/00
(52) U.S. Cl. ...................................................... 433/74
(58) Field of Search ............................. 433/34, 72, 74, 433/75

(56) References Cited

U.S. PATENT DOCUMENTS

| 3,153,283 A | 10/1964 | Weissman |
| 3,453,736 A | 7/1969 | Waltke |
| 3,969,820 A | 7/1976 | Kulig te al. |
| 4,801,264 A | 1/1989 | Weissman |
| 4,997,370 A | 3/1991 | Mayclin |
| 5,286,191 A | 2/1994 | Poveromo |
| 5,611,686 A | 3/1997 | Silva |

FOREIGN PATENT DOCUMENTS

| DE | 25 15 445 | 10/1976 |
| DE | 25 21 573 | 11/1976 |
| GB | 2 020 388 | 11/1979 |

*Primary Examiner*—Nicholas D. Lucchesi
(74) *Attorney, Agent, or Firm*—Edward M. Livingston, Esq.

(57) ABSTRACT

A coordinative dental-die-interlocking system includes a dental-die pin (1) anchored in a tooth-die base (4) and inserted removably in a die-pin sleeve (2) that is anchored in a dental-model base (6). The dental-die pin includes a pin that lock-fits in the die-pin sleeve. The dental-die pin and the die-pin sleeve include predeterminedly color-coded identification marking. A plurality of sizes of die pairs (11, 12, 13) which are color-coded mate rigidly in a system of coordinative interlocking to prevent mismatching errors and to save time matching dental-die pins and die-pin sleeves by dental artisans.

20 Claims, 3 Drawing Sheets

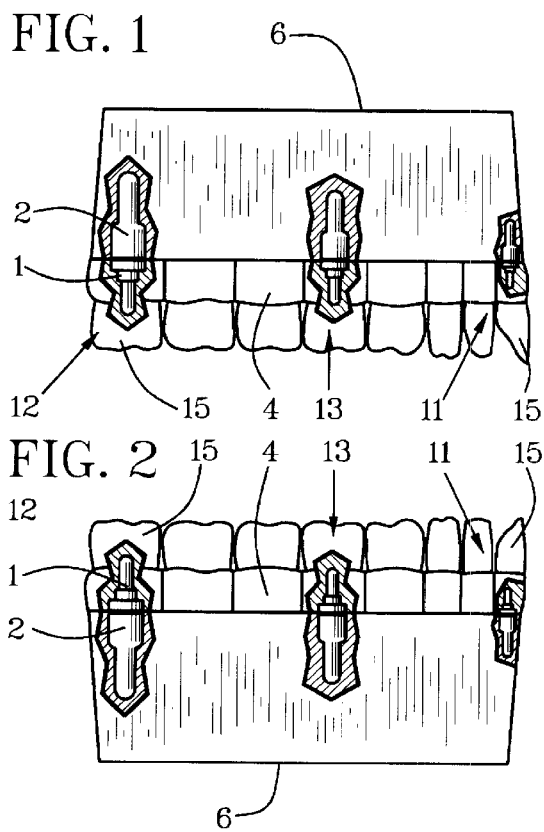
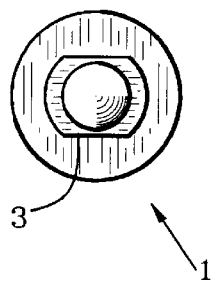
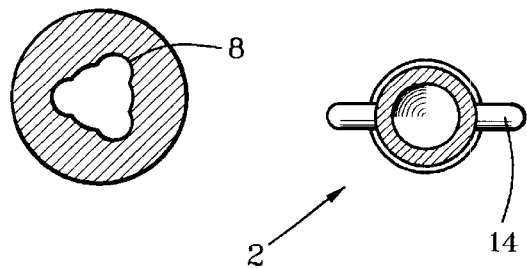
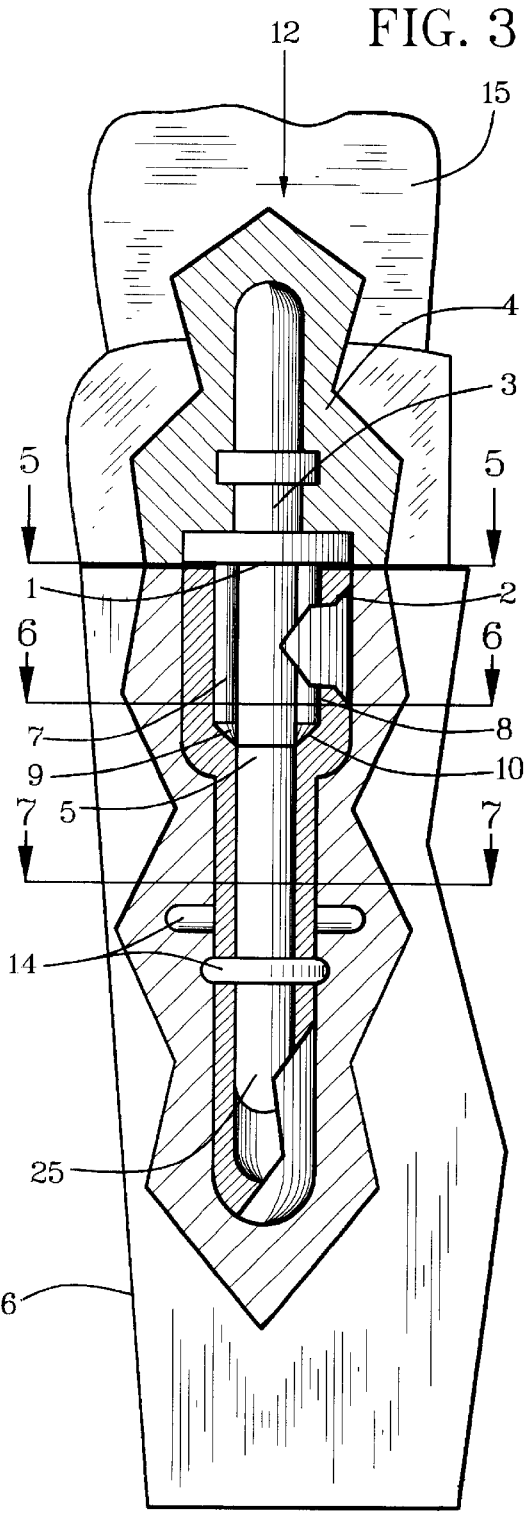

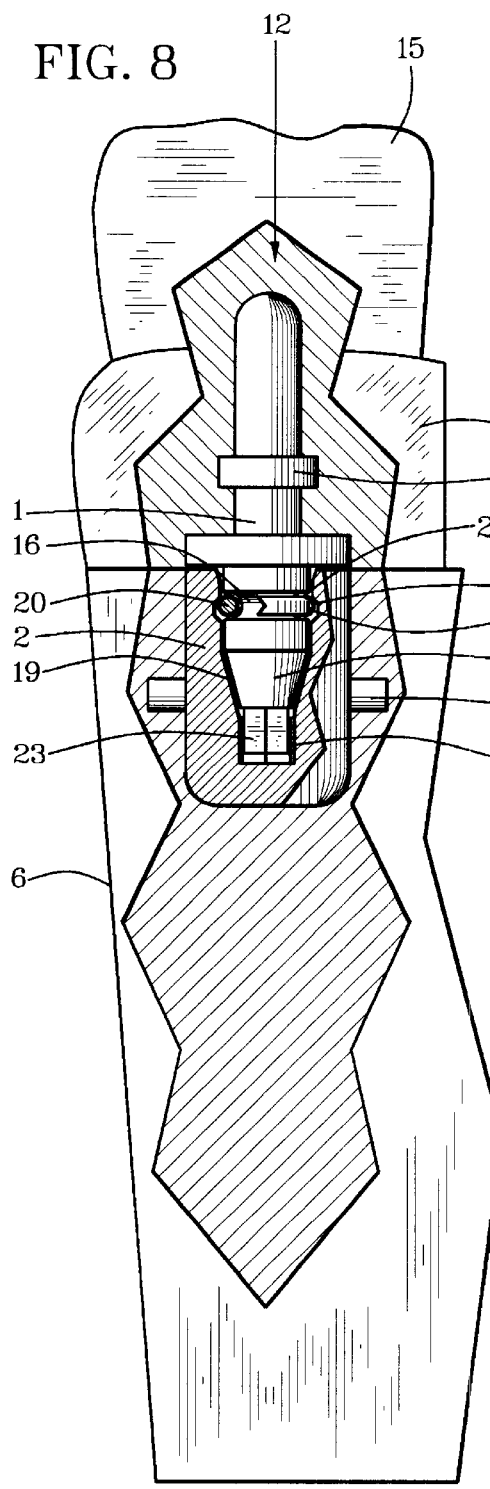
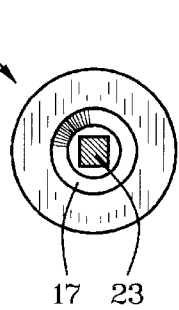
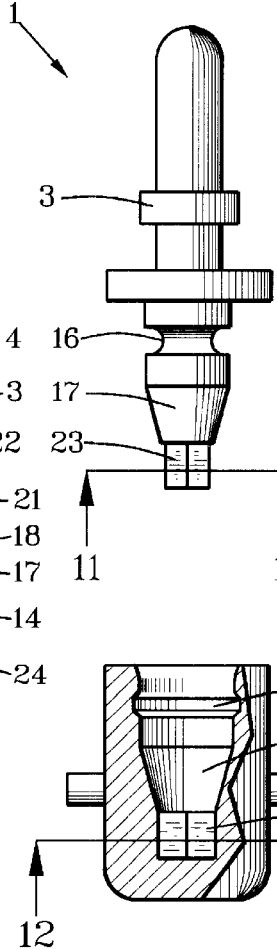
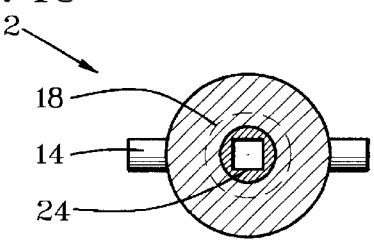
FIG. 8  FIG. 9  FIG. 11
FIG. 10
FIG. 12

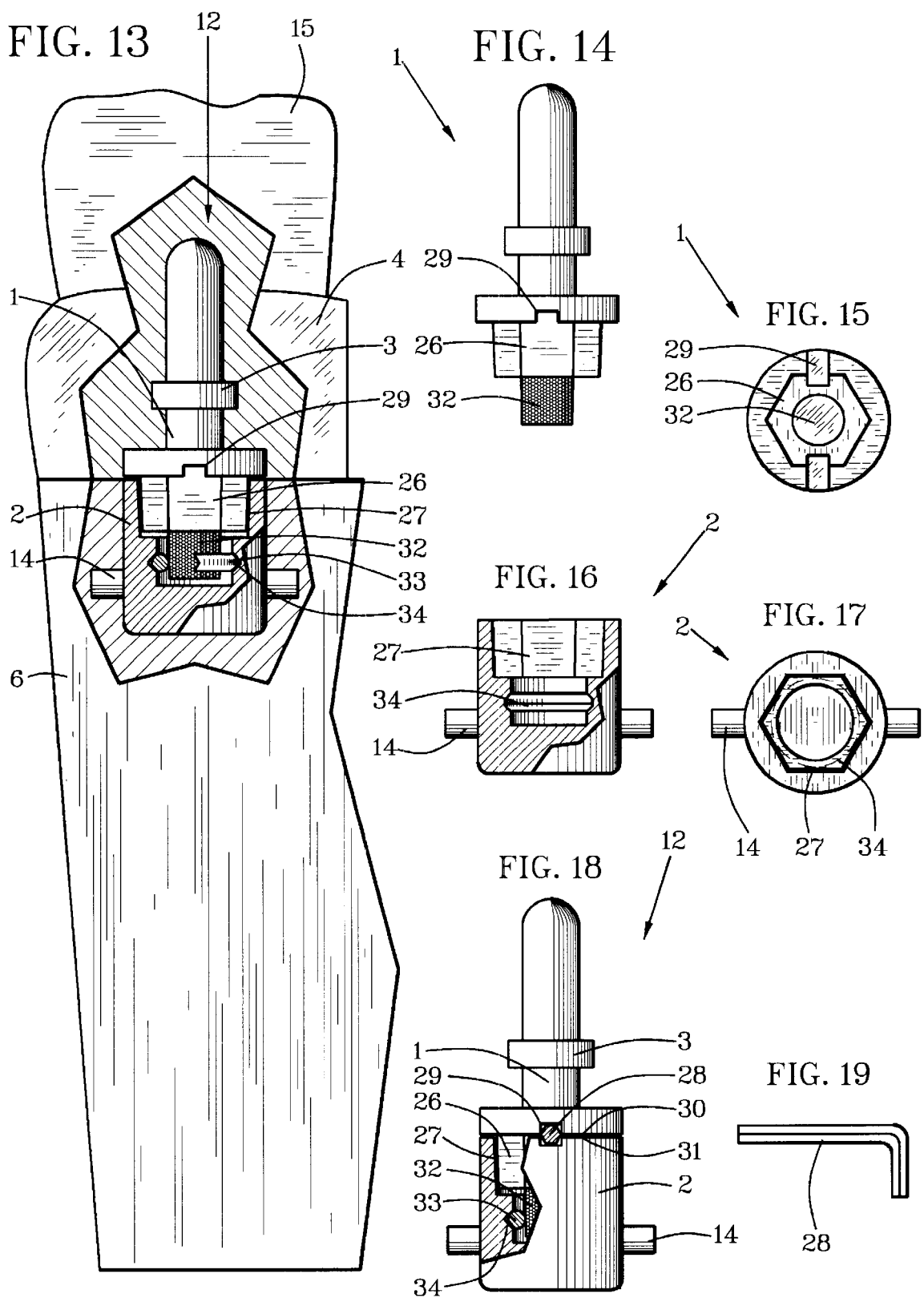

COORDINATIVE DENTAL DIE INTERLOCKING SYSTEM

BACKGROUND OF THE INVENTION

This invention relates to coordination of size, shape and color of dowel pins with sleeves for sequential preparation of dental dies related to dental prosthetics.

At present, dental tooth-die pins which hold tooth dies for being custom-shaped by dental artisans have uniform size, form and color to fit into uniformly matching die-pin sleeves on dental models. Valuable time is consumed by the dental artisans to examine tooth dies repeatedly to assure placement of tooth die pins into correct die-pin sleeves. Errors of identification and placement of the tooth dies occur frequently.

Frequently also, the tooth-die pins are not oriented accurately and held rigidly for precision shaping to dental-bite optimization.

Dentists and their patients suffer cost and human-factor consequences accordingly.

There are known tooth-die pins, sleeves and related dental systems, but not with the reliability and accuracy of tooth-die orientation, the pin-holding rigidity, the convenience of pin insertion and removal and the prevention of error of insertion of dental-die pins into die-pin sleeves taught by this invention.

Examples of most-closely related known but different dental devices and systems are described in the following patent documents:

| Patent Number | Inventor | Issue Date |
| --- | --- | --- |
| U.S. Pat. No. 5,611,686 | Silva | 03-18-1997 |
| U.S. Pat. No. 3,153,283 | Weissman | 10-20-1964 |
| U.S. Pat. No. 3,453,736 | Waltke | 07-08-1969 |
| DT 25 15 445 | Natt | 10-21-1976 |
| DT 25 21 573 | Sauter | 11-18-1978 |
| U.S. Pat. No. 3,969,820 | Kulig, et al. | 07-20-1976 |
| GB 2 020 388 | Weissman | 01-31-1979 |
| U.S. Pat. No. 4,801,264 | Weissman | 01-31-1989 |
| U.S. Pat. No. 4,997,370 | Mayclin | 03-05-1991 |
| U.S. Pat. No. 5,286,191 | Poveromo | 02-15-1994 |

SUMMARY OF THE INVENTION

Objects of patentable novelty and utility taught by this invention are to provide a dental-die pin and sleeve coordination system which:

- snap-locks dental-die pins into die-pin sleeves quickly and conveniently;
- orients the dental-die pins in the die-pin sleeves with high positioning accuracy and with high repetition accuracy in accordance with a design objective for separate teeth, for pluralities of teeth and for total dental modeling;
- holds the dental-die pins in the die-pin sleeves rigidly while being shaped, measured, analyzed and sculptured;
- prevents release of the die pins and teeth dies on them from the die-pin sleeves by tipping and upside-down orientation of bases of dental models in which the die-pin sleeves are situated;
- allows quick and easy release of the dental-die pins from the die-pin sleeves with a light pulling action; and
- prevents errors or selection of the die-pin sleeves into which the die pins containing teeth dies are inserted by dental artisans.

This invention accomplishes these and other objectives with a dental-die pin and die-pin sleeve coordinative interlocking system which includes a dental-die pin with a tooth-anchor port ion anchored in a tooth-die base and a sleeve-insertion portion inserted removably in a die-pin sleeve that is anchored in a dental-model base. The sleeve-insertion portion of the dental-die pin includes a pin section that fits designedly into a sleeve section of the die-pin sleeve, a pin-index section having one or more index projections that fit predeterminedly in one or more index receptacles in a sleeve-index section of the die-pin sleeve for receiving the index projections. The sleeve-insertion portion of the die pin includes a pin-taper section with a pin taper that fits predeterminedly in a sleeve-taper section of the die-pin sleeve and has a sleeve-taper angle that is reciprocal to a pin-taper angle. A pin lock section of the die pin includes a pin lock recess that is predeterminedly aligned with a sleeve lock recess in a sleeve lock section of a die-pin sleeve. A pin lock which includes an expansion-tensioned expandable locking member is extended intermediate the pin lock recess and the sleeve lock recess. The dental-die pin and the die-pin sleeve include predeterminedly color-coded identifier marking. A plurality of sizes of the dental-die pins which are color-coded mate with a plurality of sizes of the die-pin sleeves which are similarly color-coded in a system of coordination of dental-die pins with mating die-pin sleeves to prevent mismating errors by dental artisans.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF DRAWINGS

This invention is described by appended claims in relation to description of a preferred embodiment with reference to the following drawings which are explained briefly as follows:

FIG. 1 is a partially cutaway side view of a top dental model having three separate sizes of dental-die pins holding dental dies with die-pin sleeves in this coordinative dental-die-interlocking system;

FIG. 2 is a partially cutaway side view of a bottom dental model having three separate sizes of dental-die pins holding dental dies with die-pin sleeves;

FIG. 3 is an exploded partially cutaway side view of a rear portion of the bottom dental model containing a large size of the dental-die pin in a large size of the die-pin sleeve for detail illustration of following exploded views of the features of this invention;

FIG. 4 is a top view of the dental-die pin;

FIG. 5 is a cross-sectional view of the dental-die pin through section line 5—5 of FIG. 3;

FIG. 6 is a cross-sectional view of the die-pin sleeve through section line 6—6 of FIG. 3;

FIG. 7 is a cross-sectional view of the die-pin sleeve through section line 7—7 of FIG. 3;

FIG. 8 is an exploded partially cutaway side view of a rear portion of the bottom dental model containing an embodiment of a large size of the dental-die pin having a pin lock with an expansion-tensioned member in pin and sleeve recesses for detail illustration of following exploded views;

FIG. 9 is a side view of the FIG. 8 dental-die pin;

FIG. 10 a partially cutaway side view of the FIG. 8 die-pin sleeve;

FIG. 11 a cross-sectional bottom view of the FIG. 8 dental-die pin through section line 11—11 of FIG. 9;

FIG. 12 a cross-sectional bottom view of the FIG. 8 die-pin sleeve through section line 12—12 of FIG. 10;

FIG. 13 is an exploded partially cutaway side view of a rear portion of the bottom dental model containing an embodiment of a large size of the dental-die pin for which the pin taper is on an outside periphery of a polygonal extension of the dental-die pin axially from proximate a sleeve side of the dental-die pin, the sleeve taper is on an inside periphery of a polygonal portion of the die-pin sleeve that is proximate an entrance to the die-pin sleeve and the sleeve taper matches the pin taper;

FIG. 14 is a side view of the FIG. 13 dental-die pin;

FIG. 15 is a bottom view of the FIG. 13 dental-die pin;

FIG. 16 is a partially cutaway side view of the FIG. 13 die-pin sleeve;

FIG. 17 is a top view of the FIG. 13 die-pin sleeve;

FIG. 18 is a partially cutaway side view of an assembly of the FIG. 13 die-pin sleeve and dental-die pin showing a pry-wrench slot in which a hexagonal pry wrench is inserted; and FIG. 19 is a side view of a conventional hexagonal rod wrench for use as a pry wrench.

DESCRIPTION OF PREFERRED EMBODIMENT

Listed numerically below with reference to the drawings are terms used to describe features of this invention. These terms and numbers assigned to them designate the same features throughout this description.
1. Dental-die pin
2. Die-pin sleeve
3. Tooth-anchor portion
4. Tooth-die base
5. Sleeve-insertion portion
6. Dental-model base
7. Arcuate ridge
8. Arcuate groove
9. Tapered ridge end
10. Tapered groove end
11. First die pair
12. Second die pair
13. Third die pair
14. Sleeve anchors
15. Dental die
16. Pin groove
17. Pin-lock taper
18. Sleeve groove
19. Sleeve-lock taper
20. Resilient toroid
21. Entry-side wall
22. Insertion-side wall
23. Straight-wall
24. Straight-wall groove
25. Pin extension
26. Polygonal extension
27. Polygonal portion
28. Hexagonal-rod wrench
29. Pry-wrench slot
30. Pin wall
31. Slot wall
32. Ring-grasp extension
33. Lock ring
34. Lock-ring groove Reference is made first to FIGS. 1–7. A coordinative dental-die-interlocking system includes a dental-die pin 1 that fits conveniently, accurately and rigidly in a die-pin sleeve 2 from which it is removable easily. Fitting insertion of the dental-die pin 1 is coordinated to avoid error of insertion in incorrect die-pin sleeves 2.

The dental-die pin 1 has a tooth-anchor portion 3 for anchoring the dental-die pin 1 rigidly and permanently in a tooth-die base 4 and a sleeve-insertion portion 5 for being inserted removably in the die-pin sleeve 2.

The die-pin sleeve 2 is anchored rigidly and permanently with sleeve anchors 14 embedded in a dental-model base 6.

The sleeve-insertion portion 5 of the dental-die pin 1 includes one or more guide projections that fit predeterminedly intermediate guide walls on the die-pin sleeve 2. The one or more guide projections can include an arcuate ridge 7 shown in FIGS. 3 and 5 and the one or more guide walls can include walls of an arcuate groove 8 shown in FIGS. 3 and 6.

A pin taper on a predetermined outside peripheral portion of the dental-die-pin 1 provides rigidity of snug fitting by its bottoming snug insertion in a mating sleeve taper of the die-pin sleeve 2 that is tapered reciprocally. The pin taper can include tapering of the arcuate ridge 7 and reciprocal tapering of the arcuate groove 8. Tapering of the arcuate ridge can be end-tapering with a tapered ridge end 9 and a tapered groove end 10 as shown or optionally a full-length tapering of the arcuate ridge 7 and the arcuate groove 8 that are not shown. Taper angle can be under fifteen degrees for some embodiments and over fifteen degrees for other embodiments of this invention. Some taper angles are preferably two-to-four degrees as indicated.

To aid in coordinating insertion of the dental-die pins 1 in correct die-pin sleeves 2, a plurality of sizes of the die-pin sleeves 2, which include a separate die-pin sleeve 2 for each of a plurality of teeth sections of the dental-model base 6, is matched by a plurality of sizes of the dental-die pins 1. Preferably, the plurality of sizes of the die-pin sleeves 2 include a first sleeve size for anterior portions of dental-model bases, a second sleeve size for posterior portions of dental-model bases, and a third sleeve size for intermediate portions of dental-model bases. The plurality of sizes of the dental-die pins include a first pin size for anterior teeth, a second pin size for posterior teeth and a third pin size for intermediate teeth. The first pin size and the first sleeve size are a first die pair 11, the second pin size and the second sleeve size are a second die pair 12 and the third pin size and the third sleeve size are a third die pair 13.

The plurality of die-pin sleeves 2 include sleeve-identification markings and the dental-die pins 1 include pin-identifications which are preferably color-coded with predetermined colors on predetermined portions thereof that are visible when the die-pin sleeve 2 is separated from the dental-die pin 1.

A pin lock is in predetermined locking communication intermediate the dental-die pin 1 and the die-pin sleeve 2. In its simplest and most basic form, the pin lock is the snug fitting of the dental-die pin 1 in the die-pin sleeve 2. This can be in combination with a suitable grease-like substance to prevent the dental-die pin 1 and a dental die 15 on the tooth-die base 4 from loosening when worked on or falling out when inverted. Snugness of the fitting can be modified for particular use requirements.

Referring to FIGS. 8–12, the pin lock can include a lock recess that is a pin groove 16 extended circumferentially about an outside periphery of the dental-die pin 1 proximate a major diameter of a pin-lock taper 17. The sleeve lock recess can include a sleeve groove 18 that is extended circumferentially about an inside periphery of the die-pin sleeve 2 proximate a major diameter of a sleeve-lock taper 19. Also included for the pin lock can be a resilient toroid 20 that is an expansion-tensioned member situated predeterminedly in the pin groove 16 and in the sleeve groove 18. The sleeve groove 18 can include an entry-side wall 21 that is predeterminedly proximate an insertion-side wall 22 of the pin groove 16 while the pin-lock taper 17 is bottomed in the sleeve-lock taper 19 and while the resilient toroid 20 is in the sleeve groove 18 and in the pin groove 16 simultaneously.

The one or more guide projections can include a straight-wall ridge 23 having opposite straight walls and the one or more guide walls can include a straight-wall groove 24 having opposite straight walls. Four straight walls are shown for each but can be polygonal with as few as three but preferably less than eight straight walls.

A pin extension 25 of the dental-die pin 1 shown in FIG. 1 can be extended also from the embodiments shown in FIGS. 8 and 13 for additional pin stability and rigidity.

Referring to FIGS. 13–19, the pin taper can be on an outside periphery of a polygonal extension 26 of the dental-die pin 1 from proximate a sleeve side of the dental-die pin 1. The sleeve taper can be on an inside periphery of a polygonal portion 27 of the die-pin sleeve 2 that is proximate an entrance to the die-pin sleeve 2. The sleeve taper matches the pin taper.

For this embodiment, the pin taper preferably has predeterminedly less than seven degrees of taper angle inwardly from being parallel to an axis of the dental-die pin 1 in a direction opposite from the tooth-anchor portion 3 of the dental-die pin 1. The sleeve taper has reciprocally less than the seven degrees of taper angle outwardly from an axis of the die-pin sleeve 2. Preferably, the taper angles are two-to-four degrees.

This embodiment is particularly rigid, light weight and reliable, but sticks together so tightly, accurately and reliably that it needs to be pried apart. This can be done easily, quickly and conveniently with a pry wrench that is preferably a hexagonal-rod wrench 28 shown in FIGS. 18 and 19. A pry-wrench slot 29 is provided with slot walls that are orthogonal intermediate a pin wall 30 and a sleeve wall 31 and slot bottoms in either or both the pin wall 30 and the slot wall 31. The pry-wrench slot 29 is articulated to receive the hexagonal-rod wrench 28 snugly for its rotation to wedge against the slot bottoms for prying apart the polygonal extension 26 and the polygonal portion 27 just enough to loosen them for ease of the separation.

Optionally for this embodiment and for other embodiments, additional or supplemental grasping for effective locking of the dental-die pin 1 in the die-pin sleeve 2, can be provided with a ring-grasp extension 32 of the polygonal extension 26 or other portion of the dental-die pin 1. The ring-grasp extension 32 is circumferential with a predeterminedly slight taper. A lock ring 33 that is preferably toroidal in a lock-ring groove 34 surrounds the ring-grasp extension 32 with a predetermined snugging tightness that can be released with the hexagonal-rod wrench 28.

Although shown with this polygonal-extension 26 embodiment, this ring-grasp extension 32 is recommended more for other embodiments. This embodiment can be lighter yet with a hollowed and appropriately designed polygonal extension 26 that can be made particularly effective and convenient with the pry-wrench features, the color-coding and the plurality of sizes for this coordinative dental-die-interlocking system.

A new and useful coordinative dental-die-interlocking system having been described, all such foreseeable modifications, adaptations, substitutions of equivalents, mathematical possibilities of combinations of parts, pluralities of parts, applications and forms thereof as described by the following claims and not precluded by prior art are included in this invention.

What is claimed is:

1. A coordinative dental-die-interlocking system comprising:

a dental-die pin having a tooth-anchor portion and a sleeve-insertion portion;

the tooth-anchor portion of the dental-die pin being anchored rigidly in a tooth-die base;

the sleeve-insertion portion of the dental-die pin being inserted removably in a die-pin sleeve that is anchored rigidly in a dental-model base;

the sleeve-insertion portion of the dental-die pin including one or more guide projections that fit predeterminedly intermediate guide walls on the die-pin sleeve;

a pin taper on a predetermined outside peripheral portion of the dental-die pin;

a sleeve taper on a mating inside peripheral portion of the die-pin sleeve;

the pin taper and the sleeve taper being tapered reciprocally for snugging insertion of the pin taper in the sleeve taper, a plurality of sizes of die-pin sleeves which include a separate size of die-pin sleeve for each of a plurality of teeth sections of the dental-model base;

a plurality of sizes of dental-die pins which include a separate size of dental-die pin for each of the plurality of sizes of the die-pin sleeves;

the plurality of die-pin sleeves including sleeve-identification markings;

the plurality of dental-die pins including pin-identification markings for matching of the pin-identification markings with the sleeve-identification markings to mate the dental-die pins with the die-pin sleeves predeterminedly; and a pin lock in predetermined locking communication intermediate the dental-die pin and the die-pin sleeve.

2. The coordinative dental-die-interlocking system of claim 1 wherein:

the pin-identification markings and the sleeve-identification markings are color-coded with predetermined colors on predetermined portions thereof that are visible when the die-pin sleeve and the dental-die pin are separated.

3. The coordinative dental-die-interlocking system of claim 1 wherein:

the plurality of sizes of the die-pin sleeves include a first sleeve size for anterior portions of dental-model bases, a second sleeve size for posterior portions of dental-model bases, and a third sleeve size for intermediate portions of dental-model bases;

the plurality of sizes of the dental-die pins include a first pin size for anterior teeth, a second pin size for posterior teeth and a third pin size for intermediate teeth;

the first pin size and the first sleeve size being a first die pair;

the second pin size and the second sleeve size being a second die pair; and the third pin size and the third sleeve size being a third die pair.

4. The coordinative dental-die-interlocking system of claim 1 wherein:

the pin lock includes a pin lock recess that is predeterminedly aligned with a sleeve lock recess in the die-pin sleeve; and an expansion-tensioned locking member is extended intermediate the pin lock recess and the sleeve lock recess.

5. The coordinative dental-die-interlocking system of claim 4 wherein:

the pin lock recess includes a pin groove that is extended circumferentially about an outside periphery of the dental-die pin proximate a major diameter of a pin-lock taper; and the sleeve lock recess includes a sleeve groove that is extended circumferentially about an inside periphery of the die-pin sleeve proximate a major diameter of a sleeve-lock taper.

6. The coordinative dental-die-interlocking system of claim 5 wherein:

the pin lock includes an expansion-tensioned member that is situated predeterminedly in the pin groove and in the sleeve groove.

7. The coordinative dental-die-interlocking system of claim 6 wherein:

the expansion-tensioned member includes a circular cross section.

8. The coordinative dental-die-interlocking system of claim 7 wherein:

the sleeve groove includes an entry-side wall that is predeterminedly proximate an insertion-side wall of the pin groove while the pin-lock taper is bottomed in the sleeve taper and while the expansion-tensioned member is in the sleeve groove and in the pin groove simultaneously.

9. The coordinative dental-die-interlocking system of claim 8 wherein:

the expansion-tensioned member includes a resilient toroid.

10. The coordinative dental-die-interlocking system of claim 8 wherein:

the expansion-tensioned member includes a coil spring that is bent circumferentially into a toroidal shape intermediate proximately positioned ends of the coil spring to provide circumferentially side-tensioned resilience.

11. The coordinative dental-die-interlocking system of claim 1 wherein:

the pin taper and the sleeve taper have taper angles that are predeterminedly less than fifteen degrees from being parallel with an axis of the dental-die pin for resisting separation of the dental-die pin from the die-pin sleeve from side pressure on the dental-die pin.

12. The coordinative dental-die-interlocking system of claim 11 and further comprising:

a pry-wrench slot intermediate a base wall of a dental die on the dental-die pin and the dental-model base.

13. The coordinative dental-die-interlocking system of claim 1 wherein:

the one or more guide projections include an arcuate ridge; and the one or more guide walls include walls of an arcuate groove.

14. The coordinative dental-die-interlocking system of claim 1 wherein:

the one or more guide projections include a straight-wall ridge having straight opposite walls; and the one or more guide walls include a straight-wall groove having straight opposite walls.

15. The coordinative dental-die-interlocking system of claim 14 wherein:

the straight-wall ridge of the one or more guide projections includes a polygonal projection.

16. The coordinative dental-die-interlocking system of claim 1 and further comprising:

a pin extension of the dental-die pin extended removably into a sleeve extension of the die-pin sleeve.

17. The coordinative dental-die-interlocking system of claim 1 wherein:

the pin taper is on an outside periphery of a polygonal extension of the dental-die pin from proximate a sleeve side of the dental-die pin;

the sleeve taper is on an inside periphery of a polygonal portion of the die-pin sleeve that is proximate an entrance to the die-pin sleeve; and the sleeve taper matches the pin taper.

18. The coordinative dental-die-interlocking system of claim 17 wherein:

the pin taper has predeterminedly less than seven degrees of taper angle inwardly from an axis of the dental-die pin in a direction opposite from the tooth-anchor portion of the dental-die pin; and the sleeve taper has reciprocally less than seven degrees of taper angle outwardly from an axis of the die-pin sleeve in a direction opposite from the dental-model base.

19. The coordinative dental-die-interlocking system of claim 18 and further comprising:

a pry-wrench slot having slot walls that are orthogonal intermediate a pin wall of the dental-die pin and a sleeve wall of the die-pin sleeve; and the pry-wrench slot includes an inside periphery that is articulated to receive a predetermined polygonal-wrench rod for rotational prying to loosen the dental-die pin from the die-pin sleeve.

20. The coordinative dental-die-interlocking system of claim 18 and further comprising:

a circumferential ring-grasp extension of the polygonal extension of the dental-die pin;

the ring-grasp extension having a predeterminedly slight taper in a direction opposite from the polygonal extension;

a lock ring in a lock-ring groove in an inside periphery of a lock-ring wall of the die-pin sleeve that surrounds the ring-grasp extension; and the lock ring having an inside edge with predetermined tightness of grasping contact with the ring-grasp extension.

* * * * *